(12) United States Patent
Zhu et al.

(10) Patent No.: US 12,702,812 B2
(45) Date of Patent: Aug. 11, 2026

(54) INTRAOPERATIVE AORTIC VALVE VISUALIZATION TEST DEVICES AND SYSTEMS AND METHODS FOR USING THEM

(71) Applicant: THE BOARD OF TRUSTEES OF THE LELAND STANFORD JUNIOR UNIVERSITY, Stanford, CA (US)

(72) Inventors: Yuanjia Zhu, Stanford, CA (US); Annabel M. Imbrie-Moore, Stanford, CA (US); Michael John Paulsen, Los Altos, CA (US); Y. Joseph Woo, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 861 days.

(21) Appl. No.: 18/071,266

(22) Filed: Nov. 29, 2022

(65) Prior Publication Data

US 2023/0109069 A1 Apr. 6, 2023

Related U.S. Application Data

(63) Continuation of application No. PCT/US2021/036272, filed on Jun. 7, 2021.

(60) Provisional application No. 63/035,802, filed on Jun. 7, 2020.

(51) Int. Cl.

| | |
|---|---|
| ***A61F 2/24*** | (2006.01) |
| ***A61B 17/02*** | (2006.01) |
| ***A61M 25/00*** | (2006.01) |
| ***A61M 39/22*** | (2006.01) |

(52) U.S. Cl.
CPC ........... *A61M 39/22* (2013.01); *A61F 2/2472* (2013.01); *A61M 25/0014* (2013.01); *A61M 25/0097* (2013.01)

(58) Field of Classification Search
CPC .. A61F 2/2427; A61F 2/2472; A61B 17/3431; A61B 17/3423; A61B 2017/3429; A61B 2017/3486; A61B 2017/3425; A61B 17/34
USPC .............. 600/184; 606/194; 604/103.01, 916
See application file for complete search history.

(56) References Cited

U.S. PATENT DOCUMENTS 5,295,994 A * 3/1994 Bonutti ............... A61M 5/3286 604/164.11
5,653,705 A * 8/1997 de la Torre ........ A61B 17/3462 606/1
2003/0171713 A1* 9/2003 McFarlane ............ A61M 39/02 604/93.01
2005/0137609 A1* 6/2005 Guiraudon ......... A61B 17/3423 606/108

(Continued)

FOREIGN PATENT DOCUMENTS

EP 1943942 A1 * 7/2008 ............... A61B 5/00

*Primary Examiner* — Jessica Weiss
(74) *Attorney, Agent, or Firm* — William A. English; Vista IP Law Group LLP

(57) ABSTRACT

Devices and methods are provided for pressurization of an aortic valve of a heart before and/or after a valve surgery procedure to mimic the physiologic environment that the aortic valve experiences while allowing surgeons to visually inspect the aortic valve, so that if additional repair needs to be performed, it can be done immediately before aortotomy closure.

18 Claims, 7 Drawing Sheets

(56) References Cited

U.S. PATENT DOCUMENTS

| | | | | |
|---|---|---|---|---|
| 2007/0066943 | A1* | 3/2007 | Prasad | A61M 60/861 604/264 |
| 2008/0183283 | A1* | 7/2008 | Downing | A61F 2/2466 623/2.11 |
| 2011/0071351 | A1* | 3/2011 | Sperling | A61F 2/2472 600/101 |
| 2017/0086964 | A1* | 3/2017 | Sperling | A61F 2/2472 |
| 2020/0060819 | A1* | 2/2020 | Yamazaki | A61F 2/2472 |
| 2020/0337532 | A1* | 10/2020 | Newman | A61B 17/3421 |
| 2023/0039350 | A1* | 2/2023 | Hammer | A61B 1/3137 |

* cited by examiner

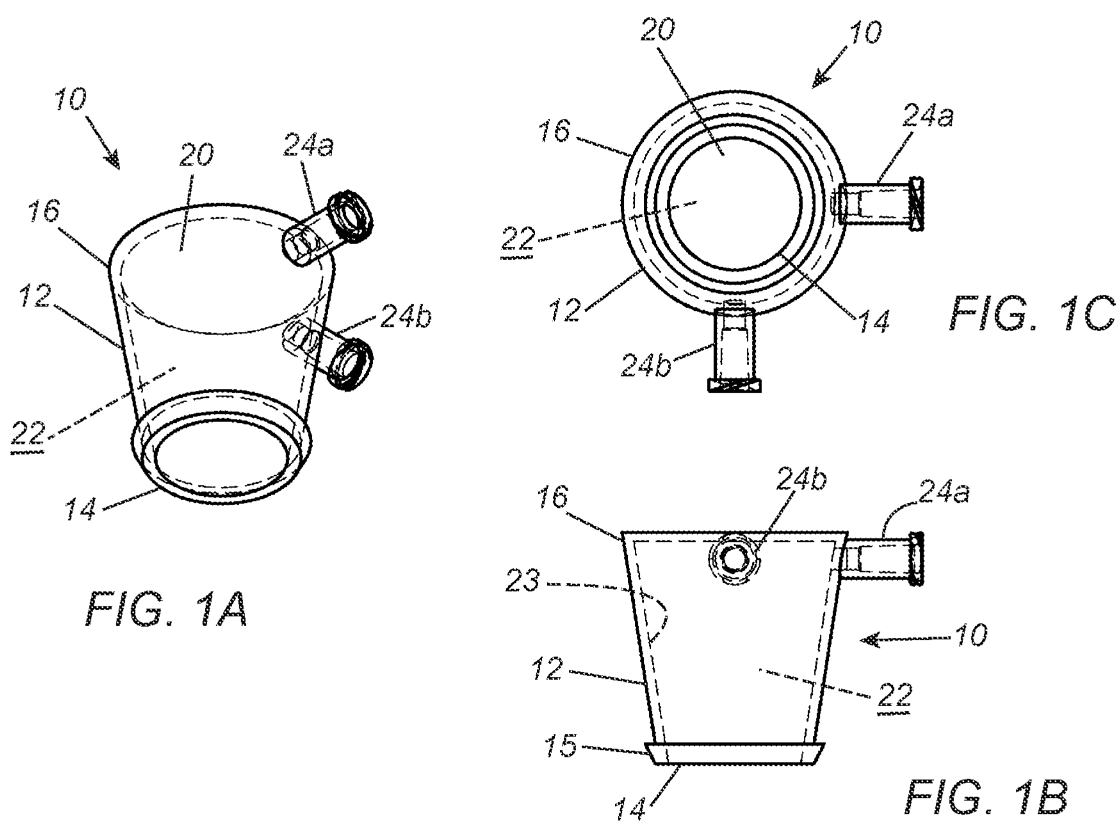
FIG. 1A
FIG. 1C
FIG. 1B
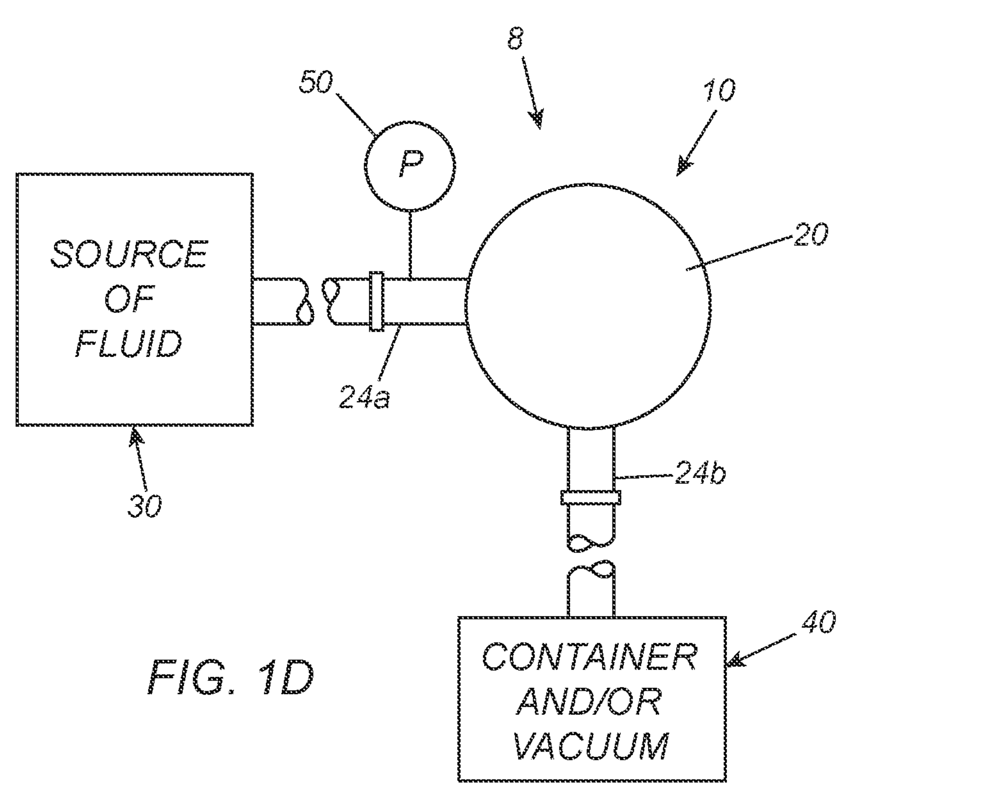
FIG. 1D

INTRAOPERATIVE AORTIC VALVE VISUALIZATION TEST DEVICES AND SYSTEMS AND METHODS FOR USING THEM

RELATED APPLICATION DATA

The present application is a continuation of co-pending International Application No. PCT/US2021/036272, filed Jun. 7, 2021, which claims benefit of U.S. provisional application Ser. No. 63/035,802, filed Jun. 7, 2020, the entire disclosures of which are expressly incorporated by reference herein.

FIELD OF THE INVENTION

The present invention relates to devices for use during medical procedures, e.g., during aortic valve repair or other surgical procedures, and, more particularly, to devices, systems, and methods for testing and/or inspecting a heart valve, e.g., an aortic heart valve before and/or after performing a valve repair or other surgical procedure.

BACKGROUND

Aortic valve surgery is a complex procedure, typically performed for patients who have aortic regurgitation and/or aortic stenosis. Aortic stenosis can be caused by congenital abnormalities and degenerative diseases, and aortic regurgitation can be caused by cusp prolapse, altered aortic root functional geometry typically due to root aneurysm, and perivalvular leak from prior aortic valve intervention, to name a few. For an aortic valve surgery, surgeons currently formulate surgical treatment strategies based on preoperative echocardiogram evidence and intraoperative findings.

Intraoperative findings are obtained from direct observation of the aortic valve after the heart is arrested and the aorta transected. The surgeon can visualize and inspect the valve and attempt to understand the etiology of aortic valve dysfunction. However, current valvular inspection can only be performed when the valve is exposed to atmospheric pressure, whereas physiologic pressure range may be required to reproduce aortic pathology. Additionally, after the aortic valve surgery is completed, there are currently no reliable, direct methodologies to visualize the valve while testing the valve functionality.

Several current approaches are used to assess valve functions prior to aortotomy closure. For example, saline can be added onto the aortic valve. If the saline level drops or if there is visible cusp prolapse, the surgeon would perform additional repair and repeat the test. This saline test, however, is extremely inaccurate. The small amount of saline added onto the aortic valve does not provide enough pressure. Hence, subtle valvular asymmetry, prolapse, and/or other defects that may not be visible from this saline test, and can manifest with significant residual aortic pathology when the valve is functioning under the physiologic pressure range.

Alternatively, surgical clamps can be used to clamp the aortic graft while fluids are injected into the graft above the aortic valve. This approach, however, is only feasible for aortic grafts. Another major limitation of this method is that the surgeon cannot directly visualize and inspect the aortic valve while the graft is being pressurized. Instead, the surgeon will have to rely on echocardiographic results, which may not be accurate given the inadequate pressure generated and poor image quality from indirect assessment.

Alternatively, the surgeon may simply squeeze the graft to estimate the pressure level generated inside the graft. If the graft seems to be under minimal pressure even though the fluid is being delivered at a high flow rate, residual aortic regurgitation is suspected, but this is an extremely inaccurate way of assessing valvular pathology.

The last option is echocardiography. Echocardiogram videos, although one of the gold-standard diagnostic tools for aortic valvular pathologies, are of low resolution. Furthermore, intraoperative assessments of the aortic valve functionality are typically performed before cardiac arrest and after completing the aortic valve surgery and aortotomy closure. Residual aortic valvular pathologies, when diagnosed, are often delayed and require the surgeon to re-cross clamp, re-arrest the heart, repeat aortotomy, and repeat aortic valve repair or replacement, all of which can significantly prolong the cardiopulmonary bypass time and aortic cross-clamp time, significantly increasing the risk of intraoperative and postoperative complications, such as stroke and heart attack.

Therefore, devices, systems, and methods that facilitate inspection and/or testing of a heart valve, e.g., an aortic valve, before and/or after a valve surgery procedure would be useful.

SUMMARY

The present invention is directed to devices for use during medical procedures, e.g., during aortic valve repair or other surgical procedures, and, more particularly, to devices, systems, and methods for testing and/or inspecting a heart valve, e.g., an aortic valve, before and/or immediately after performing a valve repair or other surgical procedure.

In an exemplary embodiment, a device is provided that allows adequate pressurization of an aortic valve of a heart before and/or after a valve procedure to mimic the physiologic environment that the aortic valve experiences while allowing surgeons to visually inspect the aortic valve before aortic valve surgery and/or before aortotomy closure. When the device is used after aortic valve surgery and before aortotomy closure, the surgeon can identify whether additional repair is necessary based on findings related to the valve function using the device; thus, the additional repair can be performed immediately without the need for cross-clamping the aorta again, arresting the heart, and re-opening the aorta.

In accordance with an exemplary embodiment, a device is provided for testing and/or visualizing a heart valve within a subject's body that includes a housing comprising one or more sidewalls extending between an open lower end sized for placement above a heart valve, and an upper end; a transparent cover enclosing the upper end of the housing for viewing the heart valve through the interior of the housing; a first port in the one or more sidewalls for connection to a source of fluid to deliver the fluid into an interior of the housing to test functionality of the valve; and one or more additional ports in the one or more sidewalls, e.g., to remove air from the interior of the housing, to perform additional diagnostic fluid injection, and/or other purposes.

In accordance with another embodiment, a system is provided for testing and/or visualizing a heart valve within a subject's body that includes a housing comprising one or more sidewalls extending between an open lower end sized for placement above a heart valve, and an upper end; a transparent cover enclosing the upper end of the housing for viewing the heart valve; a first side port in the one or more sidewalls; a source of fluid connectable to the first port to deliver the fluid into an interior of the housing to test sealing of the valve; and a second port in the one or more sidewalls to remove air from the interior of the housing displaced by the fluid delivered into the interior.

In accordance with still another embodiment, a method is provided for testing a heart valve within a subject's body that includes placing an open lower end of a housing above the heart valve, e.g., connecting the lower end to a graft or the subject's aorta such that the heart valve is visible through a transparent cover enclosing an upper end of the housing; and delivering fluid into an interior of the housing to apply pressure to the heart valve while visualizing the heart valve through the transparent cover to inspect morphology and/or functionality of the heart valve.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 1A-1C are perspective, side, and top views, respectively, of an exemplary embodiment of a device for testing and/or visualizing a heart valve during or after a surgical procedure.

FIG. 1D shows an exemplary embodiment of a system for testing and/or visualizing a heart valve using the device of FIGS. 1A-1C.

DETAILED DESCRIPTION OF THE EXEMPLARY EMBODIMENTS

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Figure 2A:
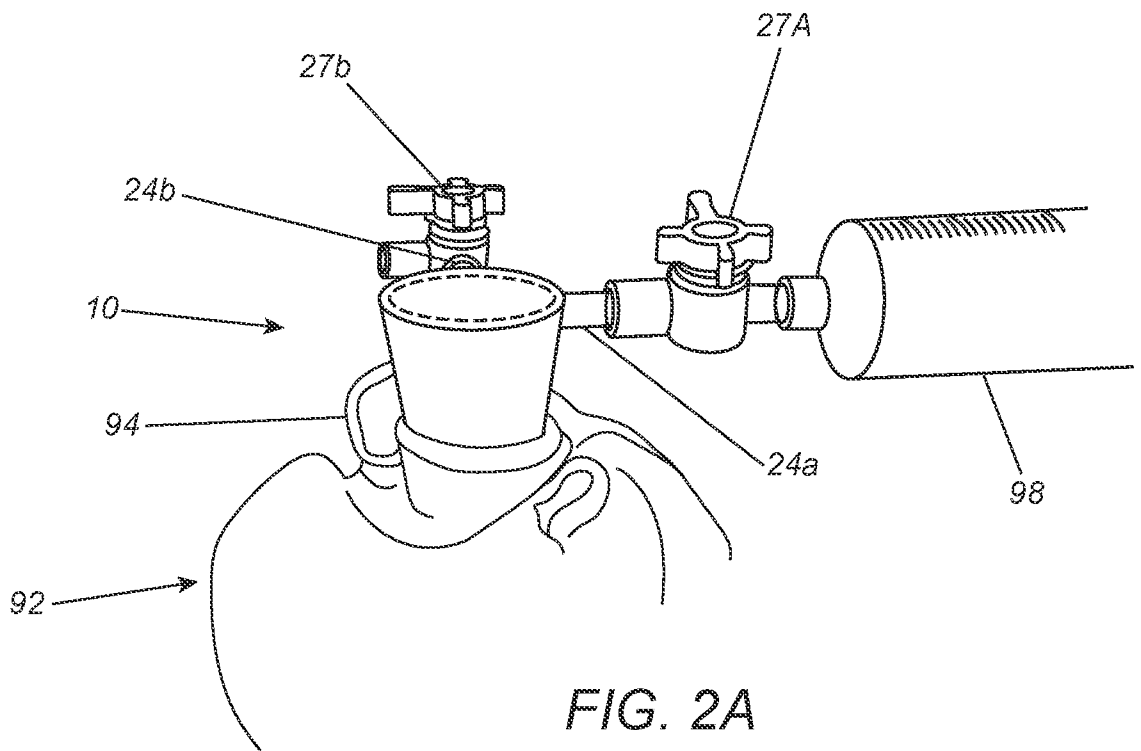
FIGS. 2A and 2B show a method for testing and/or visualizing an aortic valve using the device of FIGS. 1A-1C.
Figure 2B:
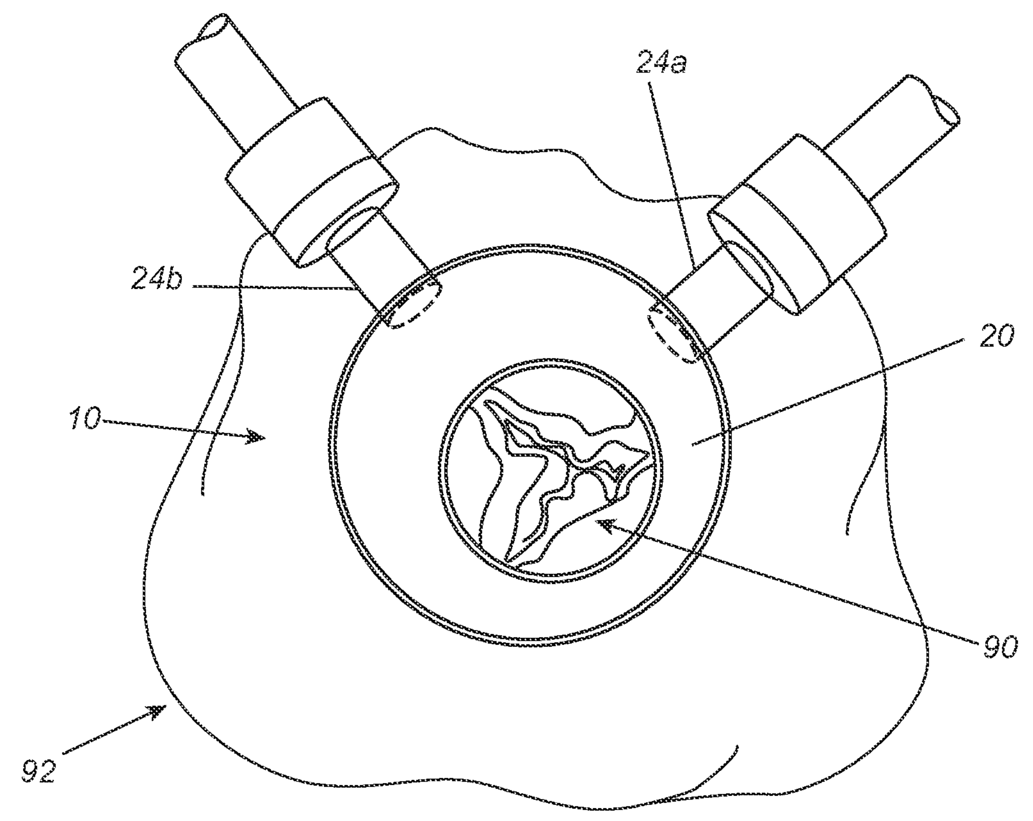

Turning to the drawings, FIGS. 1A-1C show an exemplary embodiment of a device 10 for testing and/or visualizing a heart valve, e.g., an aortic valve 90 within a heart 92 after performing a valve repair procedure, e.g., as shown in FIGS. 2A and 2B. In the embodiment shown in FIGS. 1A-1C, the device 10 includes a funnel-shaped housing 12 enclosing an interior 22 that includes an open lower end 14 and a relatively wide, upper end 16 enclosed by a transparent top or cover 20. The cover 20 may be permanently or removably attached to the upper end 16, to allow direct visualization of the aortic valve 90 through the interior 22 and open lower end 14, e.g., as shown in FIG. 2B. For example, the cover 20 may be permanently attached to one or more sidewalls 23 of the housing 12, e.g., by one or more bonding with adhesive, fusing, sonic welding, integral molding, and the like to provide a fluid-tight enclosure within the interior 22. Alternatively, the upper end 16 and cover 20 may include cooperating connectors, e.g., one or more of mating threads, tabs, detents, and the like, that allow the cover 20 to be secured to the upper end 16 with a fluid-tight fit, but allowing the cover 20 to be removed, if desired, e.g., to facilitate cleaning the device 10 and/or replacing one or more components, e.g., the cover 20. As shown, the cover 20 may be substantially flat, although alternatively the cover may have a convex, convex, or other shape (not shown), e.g., to magnify and/or otherwise enhance visualization of the valve through the device 10. Alternatively, multiple devices 10 may be provided with different shape covers, e.g., providing different levels of magnification and/or other enhancements, so that the user can select a device 10 appropriate for a particular procedure. In a further alternative, different configurations of covers may be provided that may be individually attached to a housing to provide a device with desired visualization enhancement.

Alternatively, the housing 12 may have other configurations, e.g., including a relatively large diameter upper end and a relatively small diameter lower end, e.g., sized to fit over the heart valve to be tested. The relatively large diameter upper end may facilitate observing the heart valve through the cover 20 and interior 22 from different angles. In a further alternative, the housing may define a uniform cylindrical or oblong cross-sectional shape between the upper and lower ends. In another alternative, the housing may include a plurality of sidewalls, e.g., four substantially flat or curved walls, extending between the upper and lower ends (not shown). If the housing has a square or other-non-circular cross-section, the lower end may include a circular opening or port extending from the housing sized to be connected to an aortic graft or aorta (also not shown).

The housing 12 may be formed from one or more biocompatible materials, e.g., plastic, glass, multiple composite materials having different stiffness, and the like, by molding, casting, and the like. For example, all of the components of the device 10, e.g., including the housing 12 and cover 20, may be formed from the same material. Alternatively, the device 10 may include different materials for different regions. For example, in one alternative, the lower end 14 may be formed from silicone or other elastomeric or relatively soft material, while the rest of the housing 12 is formed from rigid material. As explained further below, such softer material may provide a substantially atraumatic interface with the subject's aorta and/or other anatomy, may enhance sealing when the device is secured adjacent to a valve, and/or may be penetrable to receive needles, sutures, or other elements to secure the device 10 during use.

In one embodiment, the entire housing 12, e.g., including both the sidewall(s) 23 and cover 20, are formed from transparent material, e.g., to allow visualization of the interior 12 through the sidewall(s) and/or allow light to pass therethrough. Alternatively, the sidewall(s) 23 may be formed from translucent or opaque materials, if desired. Optionally, one or more inner surfaces of the housing 12, e.g., sidewall(s) 23, may include one or more coatings, e.g., a hydrophobic coating to prevent air bubbles from adhering the surface(s) of the housing 12 and/or otherwise facilitate de-airing and/or pressurizing the interior 22.

Figure 3:
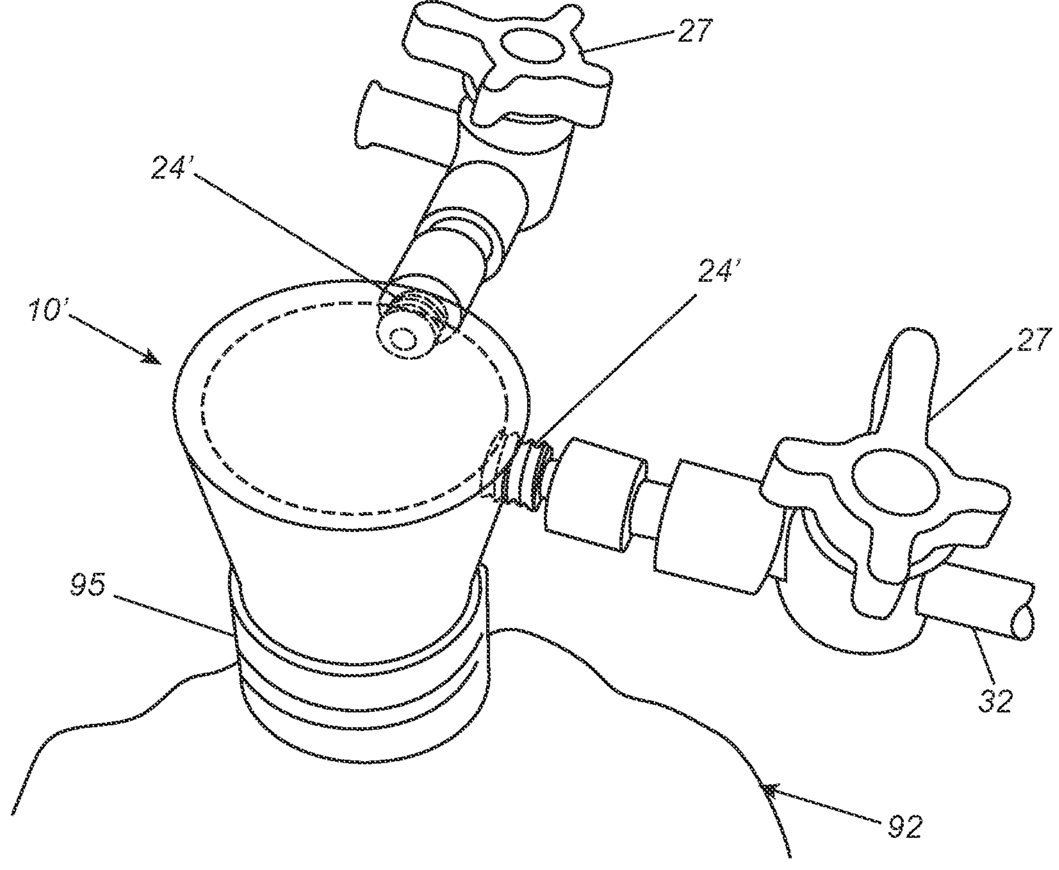
FIG. 3 shows an alternative embodiment of a device for testing and/or visualizing a heart valve.

As shown in FIGS. 1A-1C, the housing 12 includes two ports 24 in its sidewall, e.g., adjacent the upper end 16 and/or oriented substantially parallel to the surface at the cover 20. Each port 24 may include a nipple or other tubular segment 25 permanently attached to the housing 12 that may include a connector 26, e.g., a standard Luer lock fitting, a threaded connector, a ratcheted tubing connector, an annular hub, and the like, which may be connected to corresponding connectors of other devices, e.g., tubing, syringes, and the like, e.g., as shown in FIGS. 1A and 2A and described further below. Alternatively, as shown in FIG. 3, a device 10' is shown that includes two openings 24' provided in the housing instead of the ports shown in FIGS. 1A-1C. In this alternative, each opening 24' may include threads or other features designed so that commercially available connectors, e.g., Luer lock fittings, may be fitted to the housing, e.g., to provide a fluid-tight connection. Optionally, one or both ports 24 may include a valve 27, e.g., a multi-way or one-way valve including a handle to selectively open and close the fluid paths in and/or out of the interior 22, e.g., as shown in FIG. 2A. The valve 27 may be permanently or removably connected to the port(s) 24.

Alternatively, a device, such as a syringe, valve, tubing, and the like, may be coupled directly to the housing 12 to deliver fluid and/or evacuate air from the interior 22. In another alternative, two or more ports may be provided on the housing, each of which may include the same or different features, such as a nipple, connector, opening, and the like, e.g., to allow other devices to be connected to the housing (not shown).

As best seen in FIG. 1C, the ports 24 (or openings 24') may be offset from one another around a perimeter of the housing 12, e.g., offset about ninety degrees, although, alternatively, the ports 24 may be attached in other arrangements, e.g., generally opposite one another on the housing, e.g., about one hundred eighty degrees around the perimeter, or otherwise arranged on the housing 12 to facilitate manipulation and/or use of the device within a subject's chest cavity. It will be appreciated that the ports 24 may be provided at any desired locations on the housing 12, e.g., at different heights between the upper and lower ends 16, 14 of the housing 12 and/or oriented radially or tangentially, at any angle as desired, in any configuration that may facilitate use of the device 10.

The ports 24 (or openings 24') may be connected to external devices to provide a system for testing and/or visualizing a heart valve during a procedure. For example, as shown in FIG. 2A, the first port 24*a* may be connected to the outlet of a syringe 98, e.g., via a valve 27*a*, for delivering fluid into the interior 22.

Alternatively, as shown in FIG. 1D, a system 8 may be provided that includes a visualizing and/or testing device, e.g., the device 10 of FIGS. 1A-1C, a source of fluid 30, and a container or source of vacuum 40 connected by tubing 32, 34. As shown, a first port 24*a* may be connected to tubing 32 communicating with the source of fluid 30, e.g., a syringe, pump, fluid line, and the like (not shown). In an exemplary embodiment, the source of fluid may be configured to deliver saline or other biocompatible liquid, air, or other fluid or material via the first port 24 into the interior 22 of the housing 12, e.g., to fill the interior 22 and/or pressurize the heart valve 90, as described elsewhere herein.

In addition, a second port 24*b* may be connected to tubing 34 communicating with a container or, optionally, a source of vacuum, e.g., syringe, pump, vacuum line, and the like 40, e.g., to de-air the interior 22 of the housing 12 and/or facilitate visualization of the heart valve 90.

Optionally, as shown in FIG. 1D, the device 10 may include a pressure gauge or sensor 50, e.g., connected to or mounted on the first port 24 or elsewhere on the housing 12, for providing pressure measurements within the interior 22. Alternatively, the pressure sensor may be coupled to the tubing 32 and/or provided on the source of fluid 30. The pressure sensor 50 may be used during a procedure to monitor the pressure of fluid delivered into the interior 22 to test a heart valve, e.g., so that the user can deliver a desired pressure range to test performance of the heart valve under parameters similar to physiologic pressure, e.g., between about 80-120 mmHg, as described further elsewhere herein.

In the example shown in FIGS. 1A-1C, the housing 12 tapers from the upper end 16 towards the lower end 14, and the lower end 14 includes a lip 15 and/or one or more other features around its perimeter so that the end of a graft or a patient's aorta itself (not shown) may be secured onto the device 10 without slippage. For example, the lower end 14 may have a diameter such that device 10 may be connected to a wide range of graft or aorta sizes, e.g., such that tightening the graft or aorta to the lower end 14 does not distort the orientation of the aortic valve 90 relative to the transparent cover 20. In one example, the lip 15 may simply be an annular ridge molded or otherwise integrally formed in the lower end 14, e.g., including a tapered lower edge that may facilitate attachment to a graft or aorta and a blunt upper edge to resist separation during use.

Alternatively, the lower end 14 of the housing 12 may be formed from a different material, e.g., an elastic or malleable material, and/or may have other shapes to facilitate connecting the lower end to an aortic graft, aorta, or other interface. For example, as explained above, the lower end 14 may include a ring or other structure formed from silicone or other elastomeric or relatively soft material. Such material may provide a substantially atraumatic interface with the subject's aorta and/or other anatomy, e.g., to minimize damage to tissue contacted by the lower end 14. In addition, such material may enhance sealing when the device 10 is secured adjacent to a valve, e.g., to enhance a fluid-tight seal. In addition or alternatively, the material of the lower end 14 may be sufficiently soft that it may be penetrated by a needle (not shown), e.g., to allow the lower end to be secured to the aorta (or graft) using one or more sutures directed through the material and the aorta (or graft) using a needle, e.g., delivering multiple sutures between the lower end 14 and aorta (or graft) around the perimeter of the lower end 14.

Optionally, the lower end may have a tapered shape (not shown), which may facilitate using a single device to test a valve through different size openings in the aorta or different size grafts. For example, a graft or aorta may be inserted over a tapered lower end to a location where it fits snugly, and the lip may prevent the graft or aorta from sliding down or otherwise separating until the procedure is completed. Optionally, in this embodiment, there may be multiple lips or other features along the tapered lower end to serve as fixation points for the various graft or aorta sizes.

Figure 4A:
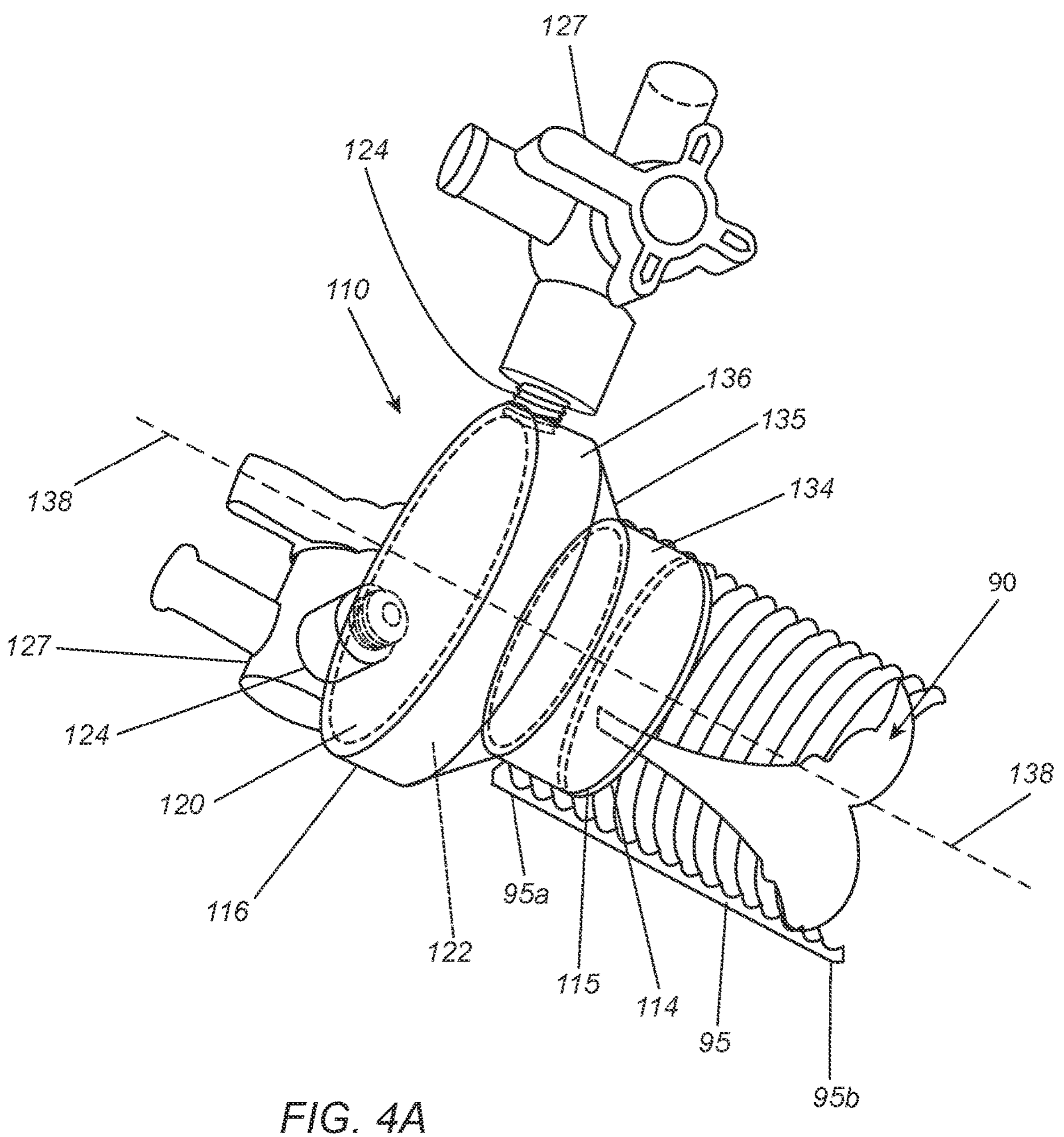
FIGS. 4A and 4B show another embodiment of a device for testing and/or visualizing a heart valve connected to a tubular graft.
Figure 4B:
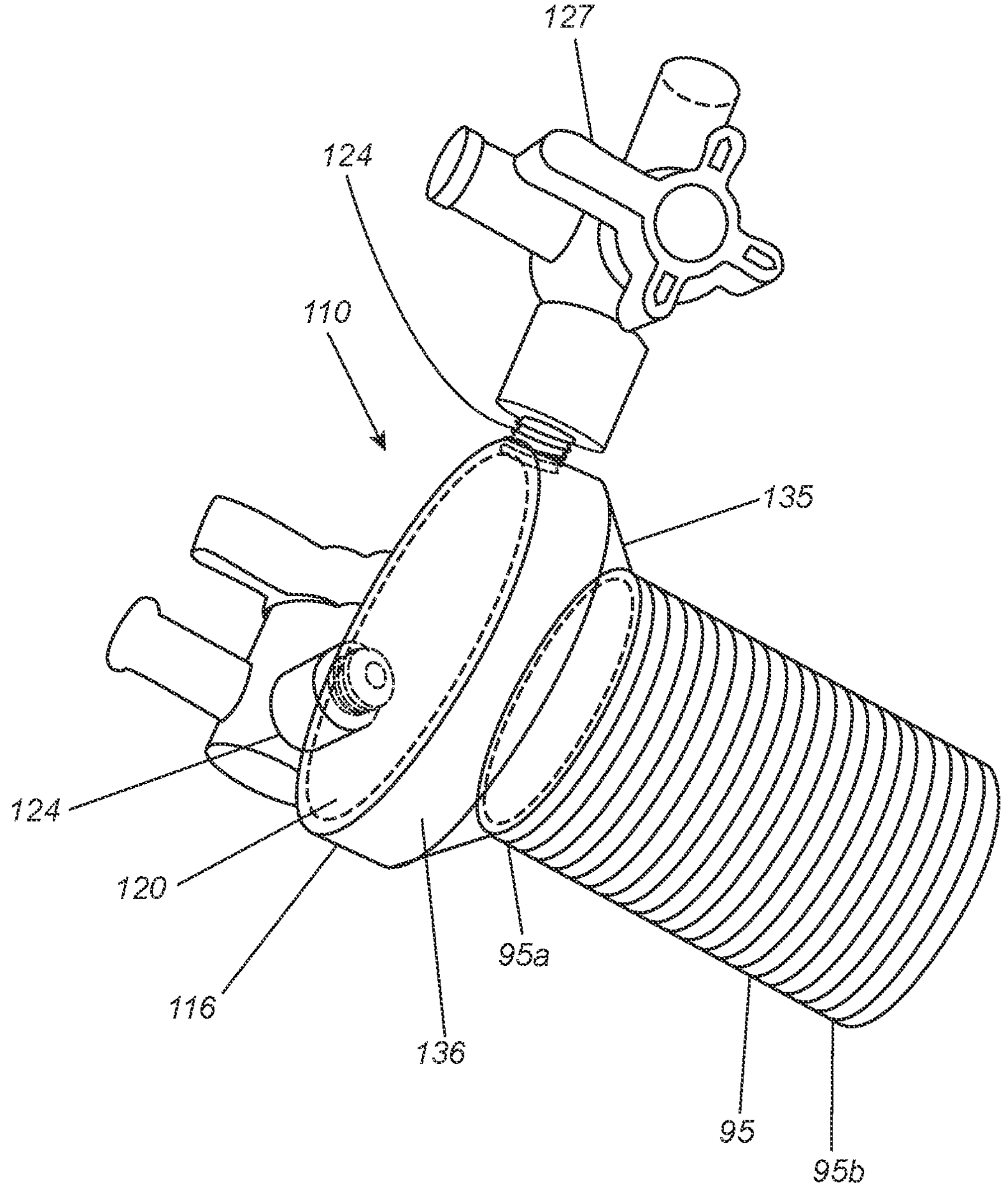
Figure 4C:
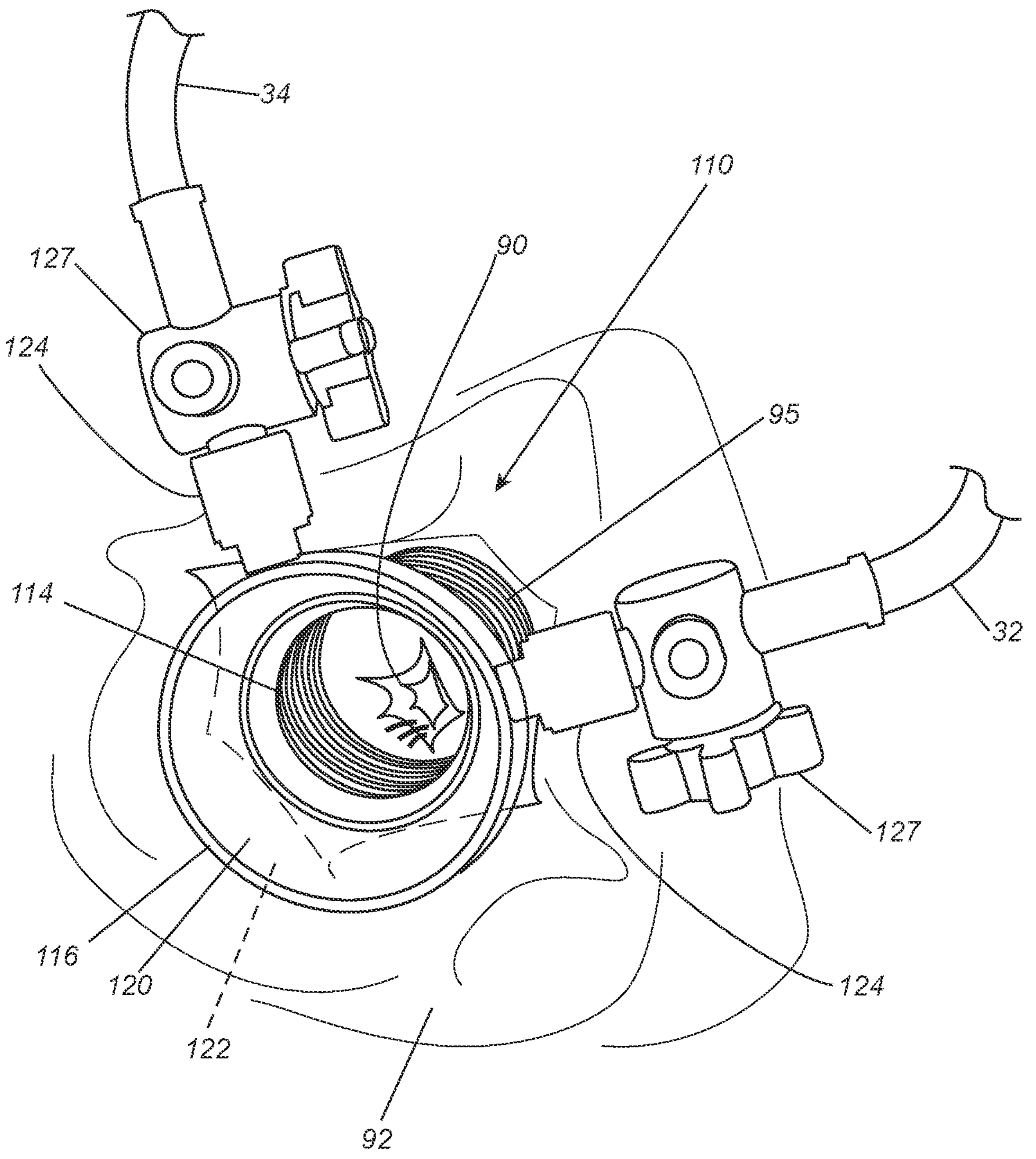
FIGS. 4C and 4D show the device of FIGS. 4A and 4B being used to visualize and/or test an aortic valve.
Figure 4D:
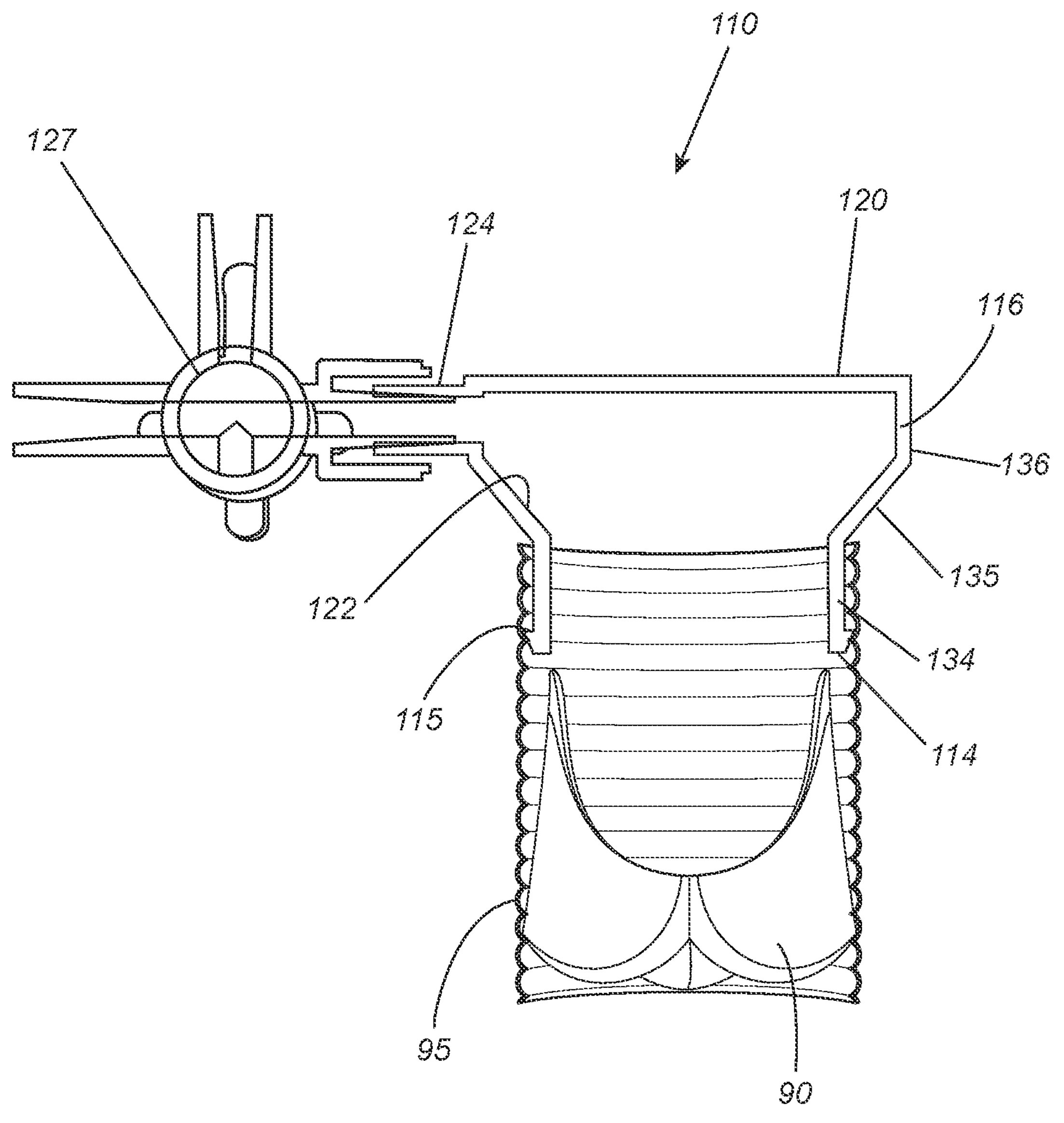

Turning to FIGS. 4A-4D, another exemplary embodiment of a visualization and/or testing device 110 is shown that generally includes a housing 112 enclosing an interior 122 that includes an open lower end 114 and an upper end 116 enclosed by a top or cover 120, similar to previous embodiments. As with other embodiments herein, at least the cover 120 is transparent to allow direct visualization of an aortic valve 90 through the interior 122 and open lower end 114, e.g., as shown in FIG. 4D. In the example shown, all of the components of the device 110, e.g., the housing 112, cover, and ports 124 are all formed from transparent material, e.g., integrally formed together from the same material.

In this embodiment, the housing 112 includes a uniform diameter lower region 134 and a uniform diameter upper region 136 connected by a tapered central region 135, e.g., concentrically around longitudinal axis 138. The upper region 136 defines a larger diameter than the lower region 134, which may facilitate observing through the cover 120 and interior 112 beyond the lower end 134 from various angles off of the axis 138, which may facilitate visualizing a valve 90 adjacent the lower end 114 without having to look directly down on the housing 112.

The upper region 136 includes a pair of ports 124, e.g., permanently mounted to the upper region 136, which may be offset around the perimeter of the upper region 136, similar to other embodiments herein. The lower end 114 includes a lip 115 and/or other features to secure the lower end to a tubular graft 95, as shown in FIGS. 4A and 4B. In addition, the device 110 may include valves 127 connected to or permanently integrated into one or both ports 124, also similar to other embodiments herein.

As shown in FIGS. 4A and 4B, a first end 95*a* of a section of tubular graft 95 may be connected to the lower end 114 that may be sized to secure a second end 95*b* of the graft 95 over or around a heart valve being tested. The graft 95 may be connected to the lower end 114 before the second end 95*b* is placed adjacent a heart valve 90 (not shown, see, FIGS. 4C and 4D), or the second end 95*a* may be secured to the patient adjacent the heart valve 90 before connecting the graft 94 to the lower end 114, as described elsewhere herein. For example, as best seen in FIG. 4A, the lower end 114 may be sized to be inserted into the first end 95*a* of the graft 95 and may include a lip 115 and/or other features to secure the graft 95 and provide a substantially fluid-tight seal.

The housing 112 may have a relatively short length (along axis 138) compared to the outer diameter of the upper end 116, e.g., such that the lower end 114 may be positioned immediate above and/or around the valve 90 and the cover 120 may be positioned a relatively short distance above the valve 90 to facilitate examination. Alternatively, a set of different size and/or shape devices may be provided, e.g., having different lengths, lower end diameters, and/or upper end diameters such that the user may select an individual device based on a particular subject's anatomy and/or the procedure being performed.

The devices and systems herein may be used in any cardiac surgery cases that involve repair of a patient's aortic valve 90, ranging from relatively more straight-forward free margin plication to complicated root surgeries, such as valve-sparing root replacement. Turning to FIGS. 2A and 2B, an exemplary method is shown for using the device 10 of FIGS. 1A-1C. For example, after completing a repair procedure and before aortotomy closure, the distal end of the patient's aorta 94 or a graft that the aortic valve 90 is attached to may be connected to the lower end 14 of the device 10.

In one example, a sterile suture may be tied around the perimeter of the lower end 14, e.g., over the lip 15, to seal the lower end 14 to an aortic graft or aorta 94. Alternatively, purse-string sutures may be placed around the aortic graft or aorta 94 after the lower end 14 is fitted inside, and then tightened around the lower end 14. In another alternative, if the lower end 14 is formed from silicone or other soft material, a needle (not shown) may be used to direct one or more sutures through the material of the lower end 14 and the adjacent graft or aorta 94, e.g., multiple times around the perimeter of the lower end 14, to secure the lower end 14 and/or tighten and provide a fluid-tight seal. In yet another alternative, sutures or the like may be wrapped around the lower end 14 one or multiple times, and then tightened to provide a fluid-tight seal.

In further alternatives, a zip-tie, clamp (with or without cushioning material), and the like (not shown) may be placed around the lip 15 or tying material and/or around the outer surface of the aorta 94 (or graft) to secure the lower end 14. Optionally, pressure feedback may be provided such that, when a predetermined threshold is reached, the tying material may be secured and any further pressure may cause the material to tear or automatically separate, e.g., to avoid damaging the aorta positioned around the lower end 14 (in addition to or instead of the connection methods just described) of the device 10. In addition or alternatively, biocompatible glue, e.g., bioglue, may be applied around the lower end 14 and/or aorta/graft to secure the aorta 94 or graft to the lower end 14 (in addition to or instead of the connection methods just described), e.g., to provide a fluid-tight seal between the device 10 and the region adjacent the valve 90.

Next, in the embodiment shown in FIG. 2A, the syringe 98 may be attached to the first port 24*a* and/or, as shown in FIG. 3, tubing 32 and/or any necessary Luer lock valves 27 communicating with the source of fluid 30 and container 40 may be attached to the ports 24.

In the embodiment shown in FIG. 2A, the second port 24*b* may include or be connected to a one-way or multi-way valve 27*b* configured to allow air to escape from the interior 12 of the device 10 as the air is displaced by fluid delivered into the housing 12. For example, a syringe 98, with or without a pressure gauge, may be coupled to the first port 24*a* and depressed to inject saline into the device 10 and residual air trapped in the device 10 may be pushed out through the second port 24*b*. Optionally, if the housing 12 includes additional ports (not shown), one or more additional fluids may be injected into the housing 12 in addition to saline or other biocompatible fluid, if desired. Once air has completely exited the device 12, the valve 27*b* may be closed to prevent further fluid flow out the second port 24*b*, and additional saline may be delivered gently via the first port 24*a* into the device 10 to pressurize the interior 12 to a desired pressure.

Alternatively, if the system 8 is used, after securing the device 10 to the subject, e.g., directly to the aorta or to a graft (not shown), any necessary tubing 32, 34 may be connected to the ports 24 and the source of fluid 30 and/or container 40. The valves 27 may be opened and fluid introduced to fill the interior 22 and displace air over the valve 90 through the port 24*b* into the container 40. Once sufficient air is displaced, e.g., with the interior 22 filled above the port 24*a*, the valve 27*b* may be closed and additional fluid delivered to pressurize the interior 22 and, consequently, the region above the heart valve 90. The pressure may be monitored using the pressure sensor 50 e.g., such that sufficient fluid is delivered to expose the valve 90 to physiologic pressure. For example, once a target pressure is achieved, the valve 27*a* of the first port 24*a* may be closed, thereby preventing delivery of additional fluid and maintaining the pressure within the interior 22 of the device 10. Alternatively, if the source of the fluid is a pump or other device with a controller, the source may be set to target pressure and, once that pressure is achieved, the pump may discontinue further fluid delivery. In this alternative, if the pressure drops below a target lower limit, e.g., due to minor leakage from the device 10, the pump may reactivate to deliver sufficient fluid to return the pressure to the target pressure and then discontinue delivery again, thereby maintaining the target pressure.

The valve 90 may then be monitored, e.g., during multiple cardiac cycles, while the valve 90 is monitored, e.g., to ensure that the leaflets coapt and/or otherwise function normally.

In particular, the device 10 may allow the surgeon to directly inspect the valve morphology and/or functionality of the valve 90 through the cover 20 and confirm whether the surgical treatment was successful, e.g., as shown in FIG. 2C. If necessary, the device 10 may be removed and additional repairs may be performed and immediately afterwards the device 10 may be reattached and the testing/visualization repeated until the repair is complete. After the valve 90 has been tested and/or observed sufficiently, the device 10 and graft (if used) may be removed and the surgical procedure completed in a conventional manner.

Thus, unlike the traditional saline test where a surgeon may just inject saline onto the surface of the aortic valve, or the clamp test where a surgeon may clamp the graft while injecting fluid into the graft, the devices, systems, and methods herein may allow the surgeon to generate adequate amount of physiologic pressure to reproduce aortic valve dysfunction that would be seen when the valve is functioning in physiologic condition.

Alternatively, rather than saline, other biocompatible liquids, for example, a crystalloid solution or biocompatible dye, may be delivered to pressurize and/or otherwise aid testing a valve, such as that disclosed in An Operative Test Device for Aortic Valve Repair, by Berra et al., The Journal of Thoracic and Cardiovascular Surgery, January 2019, pages 126-132, the entire disclosure of which is expressly incorporated by reference herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for testing and/or visualizing a heart valve within a subject's body, comprising:
- a transparent housing comprising one or more sidewalls extending between an open lower end sized for placement above a heart valve, and an upper end, the one or more sidewalls defining a peripheral outermost surface of the housing and surrounding an interior of the housing;
- a transparent cover enclosing the upper end and the interior of the housing for viewing the heart valve;
- a first port extending through the peripheral outermost surface of the housing and communicating with the interior for connection to a source of fluid to deliver fluid into the interior of the housing; and
- one or more vacuum ports extending through the peripheral outermost surface of the housing and communicating with the interior to remove air from the interior of the housing,
- wherein each of the one or more vacuum ports comprises a valve actuatable between an open position to allow air within the interior to be displaced by the fluid and a closed position to allow the fluid from the source of fluid to pressurize the interior and the heart valve.

2. The device of claim 1, wherein the one or more sidewalls comprise a cylindrical shape extending between the lower and upper ends of the housing.

3. The device of claim 1, wherein the one or more sidewalls comprise a funnel shape that tapers inwardly from the upper end to the lower end.

4. The device of claim 1, wherein the housing has a substantially uniform cross-section between the upper and lower ends.

5. The device of claim 1, wherein the housing comprises a substantially uniform cross-section upper region terminating at the upper end, and a tapered region transitioning between the upper region towards the lower end.

6. The device of claim 5, wherein the lower end has a cross-section smaller than the upper region.

7. The device of claim 1, wherein the cover is permanently attached to the upper end.

8. The device of claim 1, wherein the cover is removably attached to the upper end.

9. The device of claim 1, wherein the first port and each of the one or more vacuum ports comprise a nipple extending laterally from the one or more sidewalls.

10. The device of claim 9, wherein each nipple includes one of a Luer fitting, threaded connector, hub, ratcheted tubing connector for providing a fluid-tight connection.

11. The device of claim 9, further comprising a source of vacuum valve connected to each of the one or more vacuum ports.

12. The device of claim 1, further comprising a pressure sensor for providing pressure of fluid within the interior.

13. The device of claim 1, wherein the lower end comprises a lip extending radially around a perimeter of the lower end to facilitate removably securing the lower end to a region above the heart valve to provide a fluid-tight seal between the housing and the region.

14. The device of claim 1, wherein the valve comprises a handle movable between an open position to allow air to escape from the interior through the second port, and a closed position that closes the second port to allow the interior to be pressurized by the fluid delivered into the interior from the source.

15. A system for testing and/or visualizing a heart valve within a subject's body, comprising:

a transparent housing comprising one or more sidewalls extending between an open lower end sized for placement above a heart valve, and an upper end, the one or more sidewalls defining a peripheral outermost surface of the device and surrounding an interior of the housing;

a transparent cover enclosing the upper end of the housing for viewing the heart valve;

a first port extending through the peripheral outermost surface of the housing and communicating with the interior;

a source of fluid connectable to the first port to deliver the fluid into the interior of the housing to test sealing of the valve; and a second port extending through the peripheral outermost surface of the housing and communicating with the interior, wherein the second port comprises a valve actuatable between an open position to remove air from the interior of the housing displaced by the fluid delivered into the interior and a closed position to allow the fluid from the source of fluid to pressurize the interior and the heart valve.

16. The system of claim 15, further comprising a pressure sensor for providing pressure of fluid within the interior.

17. A method for testing a heart valve within a subject's body using the device of claim 1, comprising:

placing the open lower end of the housing above the heart valve such that the heart valve is visible through the transparent cover;

delivering liquid into the interior of the housing via the first port such that air from the interior is displaced from the interior by the liquid through the one or more vacuum ports; and closing the one or more vacuum ports and delivering additional liquid into the interior to apply pressure to the heart valve while visualizing the heart valve through the transparent cover to inspect competency of the heart valve.

18. The method of claim 17, further comprising discontinuing delivery of the liquid once a target pressure is achieved and maintaining the target pressure within the interior to allow the heart valve to be monitored during multiple cardiac cycles to ensure that leaflets of the heart valve coapt and function normally.

* * * * *